United States Patent [19]
Nakanishi et al.

[11] Patent Number: 5,959,423
[45] Date of Patent: *Sep. 28, 1999

[54] MOBILE WORK ROBOT SYSTEM

[75] Inventors: Hideaki Nakanishi, Ibaraki; Nobukazu Kawagoe, Toyonaka, both of Japan

[73] Assignee: Minolta Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/657,174

[22] Filed: Jun. 3, 1996

[30] Foreign Application Priority Data

Jun. 8, 1995 [JP] Japan .................................. 7-142048

[51] Int. Cl.⁶ .............................. B25J 5/00; G05D 1/02
[52] U.S. Cl. ............................... 318/568.12; 318/568.25; 15/319; 15/340.1; 901/1
[58] Field of Search ....................... 318/568.12, 568.24, 318/568.25, 587; 15/319, 320, 323, 327.1, 340.1–340.4, 104.8, 104.92; 134/18; 340/679, 825.06, 825.17; 901/1

[56] References Cited

U.S. PATENT DOCUMENTS

| | | |
|---|---|---|
| 4,766,432 | 8/1988 | Field . |
| 5,032,775 | 7/1991 | Mizuno et al. .......................... 318/587 |
| 5,279,672 | 1/1994 | Betker et al. . |
| 5,309,592 | 5/1994 | Hiratsuka . |
| 5,318,254 | 6/1994 | Shaw et al. ......................... 244/134 C |
| 5,377,106 | 12/1994 | Drunk et al. ....................... 364/424.02 |
| 5,402,051 | 3/1995 | Fujiwara et al. ....................... 318/587 |
| 5,440,216 | 8/1995 | Kim ...................................... 318/587 |
| 5,490,646 | 2/1996 | Shaw et al. ......................... 244/134 C |

FOREIGN PATENT DOCUMENTS

| | | |
|---|---|---|
| 5-23264 | 2/1993 | Japan . |
| 5-316605 | 11/1993 | Japan . |

*Primary Examiner*—Bentsu Ro
*Attorney, Agent, or Firm*—Burns, Doane, Swecker & Mathis, LLP

[57] ABSTRACT

The system includes a mobile work robot and a separate station. The mobile robot is equipped to perform prescribed tasks, such as cleaning building floors. The station is equipped to remotely control the movement of the mobile work robot and to perform maintenance on the mobile work robot, such as the replacement of parts as well as replenishment of consumable goods necessary for the mobile work robot to move and work. In addition, the cleaning means equipped on the station performs the cleaning and disinfection of the mobile work robot.

26 Claims, 9 Drawing Sheets

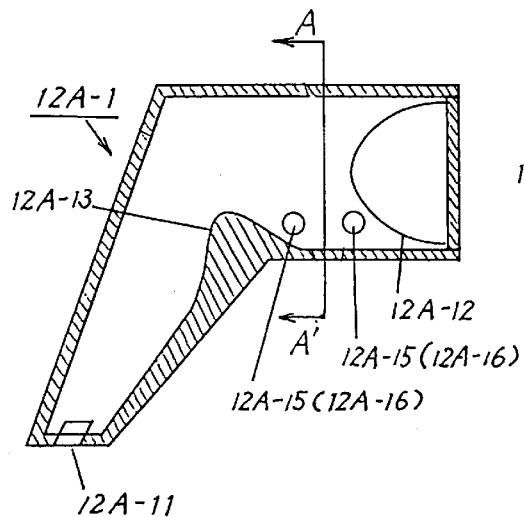
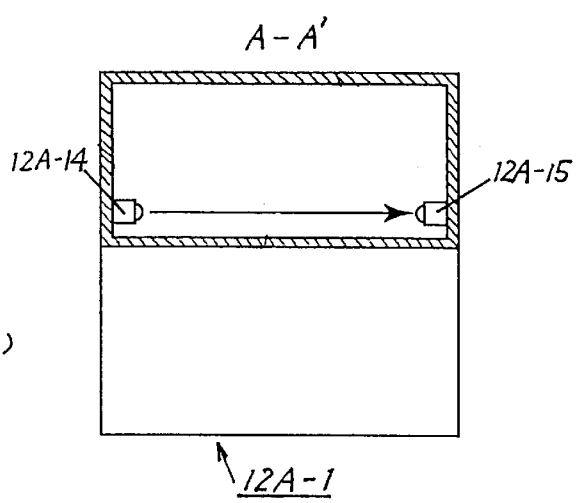
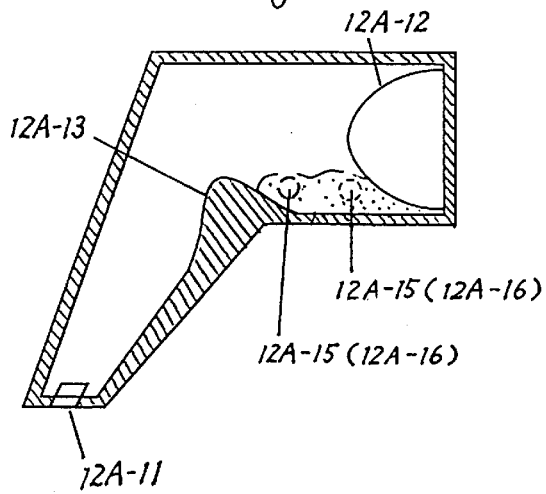

MOBILE WORK ROBOT SYSTEM

BACKGROUND OF THE INVENTION

1. Field of the Invention

The present invention pertains to a mobile work robot system that performs tasks while moving, and more particularly, to a mobile work robot system that is used in hospitals, clean rooms, etc., where microorganisms, trash, dust, etc. are to be prevented from entering and, if they enter, are to be removed.

2. Description of Related Art

In a conventional mobile work robot system, one robot performs all the functions to be performed such that one robot provides a complete and independent system. Further, maintenance of the mobile work robot, such as cleaning and disinfection, replacement of parts, and replenishment of consumable goods, is manually performed.

However, using a conventional mobile work robot system described above, it is necessary for the robot to carry large amounts of consumable goods required for the work in order for the robot to be able to work over a large area and with a long time between replenishment of the consumable goods. Further, where dust collection is performed, for example, the dust container must be made large as well. In addition, the moving means, such as wheels, that supports the robot and what it carries must be made strong. For these reasons, mobile work robots have become quite large, making them difficult to use in small areas.

If the main unit of a mobile work robot is reduced in size, maintenance tasks such as the replacement of parts and replenishment of consumable goods must be performed more frequently. Therefore, in addition to the increased cleaning and disinfection of the mobile work robot main unit, a worker who carries out these tasks must perform an increased amount of work. Furthermore, in the case of a mobile work robot that works in areas where microorganisms, trash, dust, etc. are unwanted, there is a danger that the worker who performs cleaning and maintenance of the mobile work robot will contaminate the robot.

As another type of mobile work robot system, a system having an unmanned vehicle equipped with a power supply unit and a station equipped with a replacement power supply unit has been proposed in Japanese Unexamined Laid-Open Patent Hei 5-316605, for example. In this system, replacement of the power supply unit can be achieved without human contact. In addition, since the power supply unit mounted on the unmanned vehicle can be regularly replaced at the station, the power supply unit does not have to be so large and the vehicle can be made more compact.

However, in the system described above, the station only replaces the power supply unit of the unmanned vehicle. Control functions, such as the issuance of instructions from the station when necessary to move the vehicle to the station, may not be performed.

Moreover, Japanese Unexamined Laid-Open Patent Hei 5-316605 does not provide any consideration of the cleaning (disinfection) of the unmanned vehicle.

SUMMARY OF THE INVENTION

An object of the present invention is to provide a mobile work robot that is reduced in size compared to prior mobile robots performing the same functions, as well as a mobile work robot system with a simple construction that is automated such that the maintenance of the mobile work robot main unit need not be manually performed.

Another object of the present invention is to provide a mobile work robot system that is automated such that the cleaning of the mobile work robot main unit need not be manually performed.

In order to achieve these and other objects, the mobile work robot system of the present invention has a mobile work robot equipped with moving means and working means that performs prescribed tasks, as well as a station that is constructed separately from the mobile work robot and that is equipped with control means that controls the moving means of the mobile work robot and maintenance means that performs maintenance of the mobile work robot, wherein maintenance of the mobile work robot is performed by the maintenance means.

The mobile work robot system of the present invention also has a mobile work robot equipped with a moving means and a working means that performs prescribed tasks, and a station that is constructed separately from the mobile work robot and that is equipped with cleaning means that performs the cleaning of the mobile work robot, wherein cleaning of the mobile work robot is performed by the cleaning means.

Using the construction of the present invention, the maintenance means equipped on the station to perform control of the moving means of the mobile work robot performs replacement of parts as well as replenishment of consumable goods necessary for the mobile work robot to move and work.

In addition, the cleaning means equipped on the station performs the cleaning and disinfection of the mobile work robot.

BRIEF DESCRIPTION OF THE DRAWINGS

The invention will now be described by way of exemplary embodiments with reference to the accompanying drawing figures, in which:

FIGS. 10(A)–10(C) are drawings of the dust container in accordance with the present invention.

DETAILED DESCRIPTION OF THE PREFERRED EMBODIMENTS

Embodiments of the present invention are explained below, with reference to an example in which the mobile work robot (hereinafter simply called the 'robot') cleans building floors.

Figure 1:
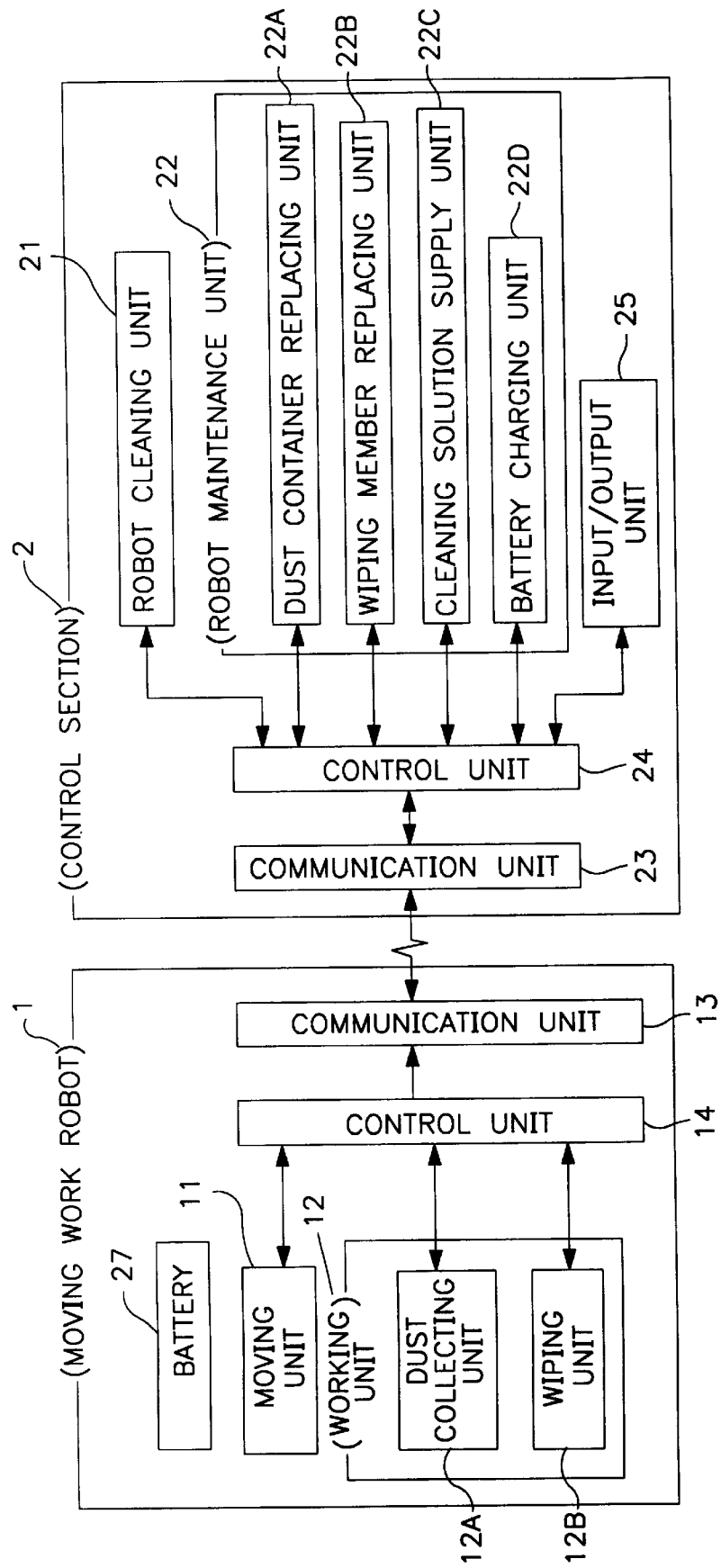
FIG. 1 is a block diagram showing the construction of the mobile work robot system in accordance with the present invention.
Figure 2:
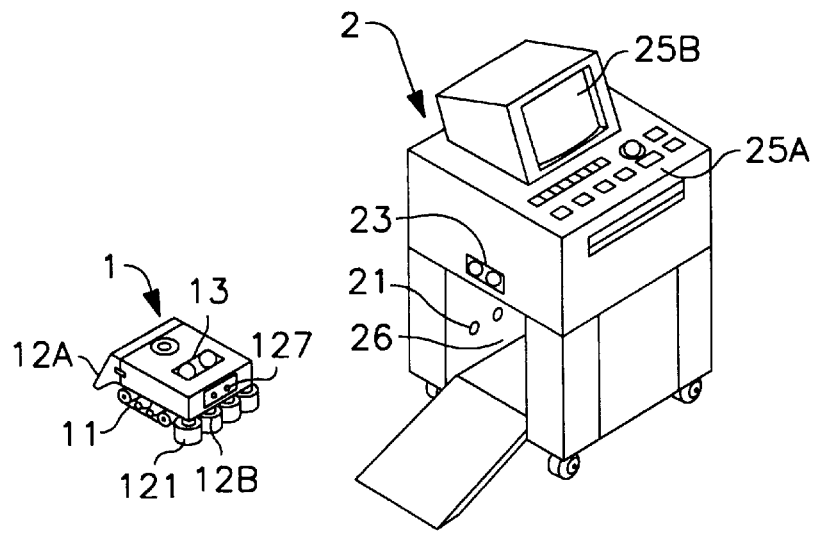
FIG. 2 is a drawing showing a mobile work robot system in accordance with the present invention.

FIG. 1 is a block diagram showing the construction of a mobile work robot system and FIG. 2 is a perspective view thereof. The mobile work robot system of this embodiment comprises a robot 1 and a control section 2 that is constructed separately from the robot 1. The robot 1 actually moves on and cleans a floor. A control section 2 works as a service station for the robot 1.

The robot 1 has a moving unit 11, a working unit 12, a communication unit 13 and a control unit 14. The moving unit 11 includes wheels and rotational angle detectors (not shown in the drawings). Two or more wheels are mounted on either side of the bottom of the robot 1. The wheels on either side have independent motors which are independently driven and controlled by the control means 14. The robot 1 moves on the floor under the power of the motors the rotation of which are transmitted to the floor through the wheels. The rotational angle detectors are linked to the wheels, and detect the rotational angles of the wheels. The rotational angle detector consists of a photosensor and a pulse encoder comprising an encoder plate that is attached to a wheel. These rotational angle detectors are connected to a microcomputer of the control unit 14 so that the output from the photosensors is input into the microcomputer. Crawlers may be used in place of the wheels.

The working unit 12 is equipped with a dust collecting unit 12A and a wiping unit 12B. The dust collecting unit 12A has a vacuum unit (not shown in the figures) and a dust container 12A-1 (FIGS. 10(A)–10(C)). The vacuum unit sucks in trash and dust from the floor. The dust container 12A-1, as shown in FIGS. 10(A) and 10(B), has a inhalation portion 12A-11, a filter 12A-12 and a bank portion 12A-13. The trash and dust sucked in from the inhalation portion 12A-11 by the vacuum unit are kept back by the filter 12A-12 and fall between the filter 12A-12 and the bank portion 12A-13. The bank portion 12A-13 is for preventing the trash and dust from falling toward the inhalation portion 12A-11. Furthermore, two sets of dust collection sensors, each of which is comprised with a light emitting element 12A-14 and a light receiving element 12A-15, are provided on the inner walls of the container 12A-1 to detect the amount of trash and dust in the container 12A-1. The dust collecting sensors are connected to the microcomputer of the control unit 14. As shown in FIG. 10(C), when the dust collection sensors detect that the amount of trash and dust inside the dust container 12A-1 has exceeded a prescribed level, it outputs an excess collected dust warning signal to the control unit 14. The dust container 12A-1 is replaceably mounted as described below.

The wiping unit 12B is equipped with a tank and wiping members 121 (FIG. 2). The tank houses solution such as a disinfectant, and drops the solution onto the floor as necessary. The wiping members 121 comprise sponge-like members, for example, and spread the solution released onto the floor and wipe the floor. The wiping unit 12B has first and second solution level sensors that detect the amount of the solution inside the tank. These sensors are connected to the microcomputer of the control unit 14. The first solution level sensor is mounted on the side and near the bottom of the tank. When it detects that the amount of solution inside the tank is less than a prescribed level, it outputs a solution amount insufficient warning signal to the control unit 14. The second solution level sensor is placed on the side and near the top of the tank. When it detects that the amount of solution inside the tank exceeds a prescribed level, it outputs a solution full signal to the control unit 14.

A communication unit 13 has a light emitting unit and a light receiving unit and sends and receives signals to and from a communication unit 23 of the control section 2 via infrared communication, for example, upon receiving control signals from the control unit 14.

The control unit 14 comprises a microcomputer to which a ROM and a RAM, for example, are connected. The microcomputer directly controls the moving unit 11, the working unit 12 and the communication unit 13 in accordance with programs stored in the ROM. Procedures executed by the microcomputer include control of the operations of the moving unit 11 and the working unit 12 in response to instruction signals sent from the control section 2 and control of the communication unit 13 so that various request signals are sent to the control section 2 based on signals from various sensors mounted on the robot 1. The RAM is used as a work area in which various types of data are stored.

The control section 2 has a robot cleaning unit 21, a robot maintenance unit 22, the communication unit 23, a control unit 24 and an input/output unit 25. It also has shed or enclosure 26.

The robot cleaning unit 21 includes a spray device, for example. The spray device sprays the cleaning solution (detergent, disinfectant, etc.) stored in the tank 21-1 (FIGS. 11(A)–11(C)) of the spray device onto the robot 1 when housed in the shed 26. The spraying of the disinfectant is performed such that it is sprayed onto the robot 1 from the top, bottom, left and right. Part of the floor of the shed 26 is formed of netting or the like such that the cleaning solution may be sprayed onto robot 1 from underneath through the netting. The entire robot 1 becomes completely cleaned and disinfected after traveling over a short distance inside the shed 26.

Figure 11A:
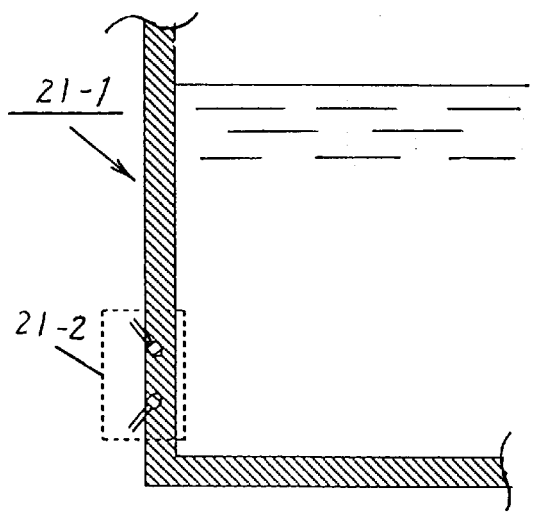
FIGS. 11(A)–11(C) are drawings of the tank of the spray device in accordance with the present invention.
Figure 11B:
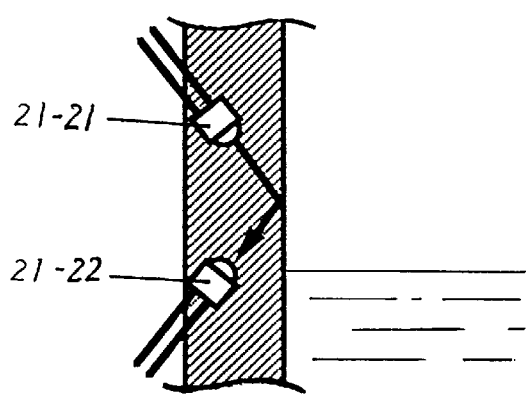
Figure 11C:
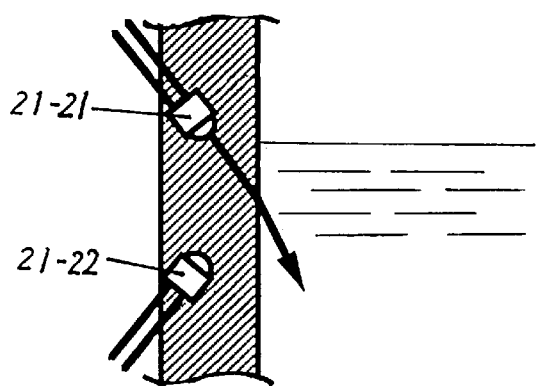

As shown in FIGS. 11(A)–11(C), the tank 21-1 of the spray device has a solution level sensor 21-2, which has the same construction of the first and second solution level sensors of the wiping unit 12B, to detect the amount of cleaning solution present. This sensor 21-2 is provided in a wall of tank 21-1 which is transparent, and is comprised with a light emitting element 21-21 and a light receiving element 21-22. As shown in FIGS. 11(B) and 11(C), this sensor 21-2 uses a change of reflection characteristics of the wall to detect the level of the solution. When the level of the solution is lower than the position of the sensor (FIG. 11(B)), the surface of the wall reflects the light from the light emitting element 21-21 and the light is detected by the light receiving element 21-22. On the other hand, when the level of the solution is higher than the sensor 21-2 (FIG. 11(C)), the surface of the wall refracts the light but does not reflect it, and the light is not detected by the light receiving element 21-22. As understood from above, the output from the light receiving element is changed in accordance with the level of the solution. This sensor is connected to the microcomputer of the control unit 24. When the solution level sensor detects that the cleaning solution inside the tank is below a prescribed level, it sends a solution amount insufficient signal to the microcomputer.

Where the purpose of the robot cleaning unit 21 is disinfection (sterilization, in particular) of the robot 1, an ultraviolet ray irradiation device could be used in place the cleaning solution spray device. The robot cleaning unit 21 may also be comprised of both a cleaning solution spray device and an ultraviolet ray irradiation device.

The robot maintenance unit 22 has a dust container replacing unit 22A, a wiping member replacing unit 22B, a cleaning solution supply unit 22C and a battery charging unit 22D, shown in FIG. 1. The dust container replacing unit 22A replaces the dust container mounted in the dust collecting unit 12A of the robot 1. The wiping member replacing unit 22B replaces the wiping members 121 mounted in the wiping unit 12B. The cleaning solution supply unit 22C supplies cleaning solution to the tank in the wiping unit 12B. The battery charging unit 22D charges a battery 27 that is the power source for the operation of the robot 1 and is built into the robot 1. These units will be explained in detail below.

A communication unit 23 has a light emitting unit and a light receiving unit. The communication unit 23 sends and receives signals to and from the communication unit 13 of the robot 1 via infrared communication.

The control unit 24 comprises a microcomputer to which a ROM and RAM, for example, are connected. The microcomputer controls the communication unit 23 according to programs stored in the ROM so that instruction signals are sent to the robot 1. The microcomputer also sends to the communication unit 13 of the robot 1 via the communication unit 23 instruction signals to control the moving unit 11 and the working unit 12 based on request signals sent from the robot 1. The RAM is used as a work area in which various types of data are stored.

An input/output unit 25 has an operation panel 25A and a display unit 25B. The operation panel 25A has multiple keys, and the user gives instructions to the control section 2 by operating these keys. The display unit 25B includes a CRT display, for example, and displays various information regarding the control section 2 and the robot 1.

The communication between the robot 1 and the control section 2 will now be explained. In the mobile work robot system of this embodiment, the robot 1 moves and works in accordance with instruction signals from the control section 2. Signals from the control unit 24 of the control section 2 are sent by means of the communication unit 23 and are received by the communication unit 13 of the robot 1. They are then sent to the control unit 14. Conversely, signals from the control unit 14 of the robot 1 are sent by means of the communication unit 13 and are received by the communication unit 23 of the control section 2. These signals are then sent to the control unit 24. While it is assumed that the two communication units 13 and 23 perform wireless communication such as infrared communication in this embodiment, they can be made as wired communication devices.

The control of the moving unit 11 will be explained as an example. The control unit 24 of the control section 2 obtains information regarding the current position of the robot 1, i.e., coordinate information, from the control unit 14 of the robot 1. The control unit 24 sends information regarding the next target position, i.e., coordinate information, to the control unit 14 based on this current position information. Receiving this information, the control unit 14 operates the motors of the moving unit 11 at variable speeds by means of PWM (pulse width modulation) signals. In other words, the control unit 14 calculates the actual angular speeds of the wheels based on the information regarding the rotational angles obtained through the input from the rotational angle detectors.

Based on the angular speeds thus calculated, the control unit 14 sends feedback to the voltage waveforms (PWM signals) applied to the motors so that the wheels attain prescribed angular speeds. At the same time, the control unit 14 calculates the travel distance of the robot 1, updates positional information in the control unit 14 and continues control so that the robot 1 reaches the target position. As described above, the left and right motors are controlled independently of each other.

The control unit 14 of the robot 1 determines at prescribed intervals whether or not maintenance is needed while the robot 1 is performing tasks. The counting of time is performed using a timer built into the microcomputer of the control unit 14. Specifically, the control unit 14 calls the routine of determination regarding the need for maintenance through an interrupt process at prescribed intervals.

Figure 8:
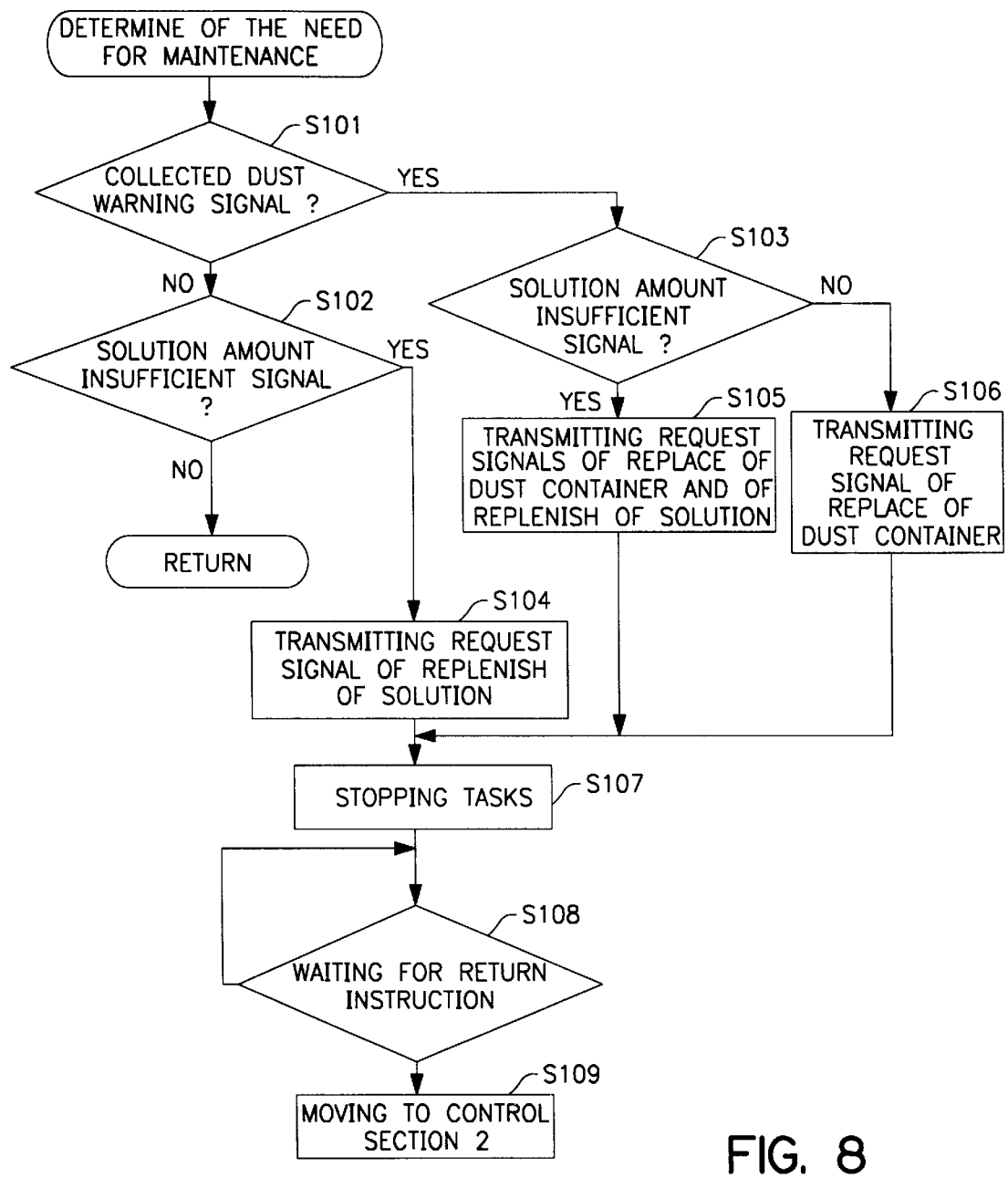
FIGS. 8 and 9 are flowcharts showing the operation of the present invention.

FIG. 8 shows the sequence of the routine regarding the determination of the need for maintenance. That is, it is determined whether an excess collected dust warning signal has been input from the collected dust level sensor and a solution amount insufficient warning signal has been input from the solution level sensor (steps S101, S102, S103). Where neither of the warning signals has been input, the sequence of this routine comes to an end. Where one or both of the warning signals has been input, a signal requesting maintenance is sent to the control section 2 through the control of the communication unit 13 (steps S104 through S106). After the signal requesting maintenance is sent, movement and performance of tasks by the robot 1 are stopped (step S107) and the robot 1 waits for a return instruction from the control section 2 (step S108). Upon receiving a return instruction from the control section 2, the robot 1 moves to the control section 2 through the control of the moving unit 11 (step S109). In the control unit 24 of the control section 2, when the request for maintenance is received from the control unit 14, the current condition of the robot maintenance unit 22 is checked, and where maintenance can be performed, a routine to send the robot 1 an instruction to move to the station is carried out. Specifically, the routine shown in FIG. 9 is performed.

Figure 9:
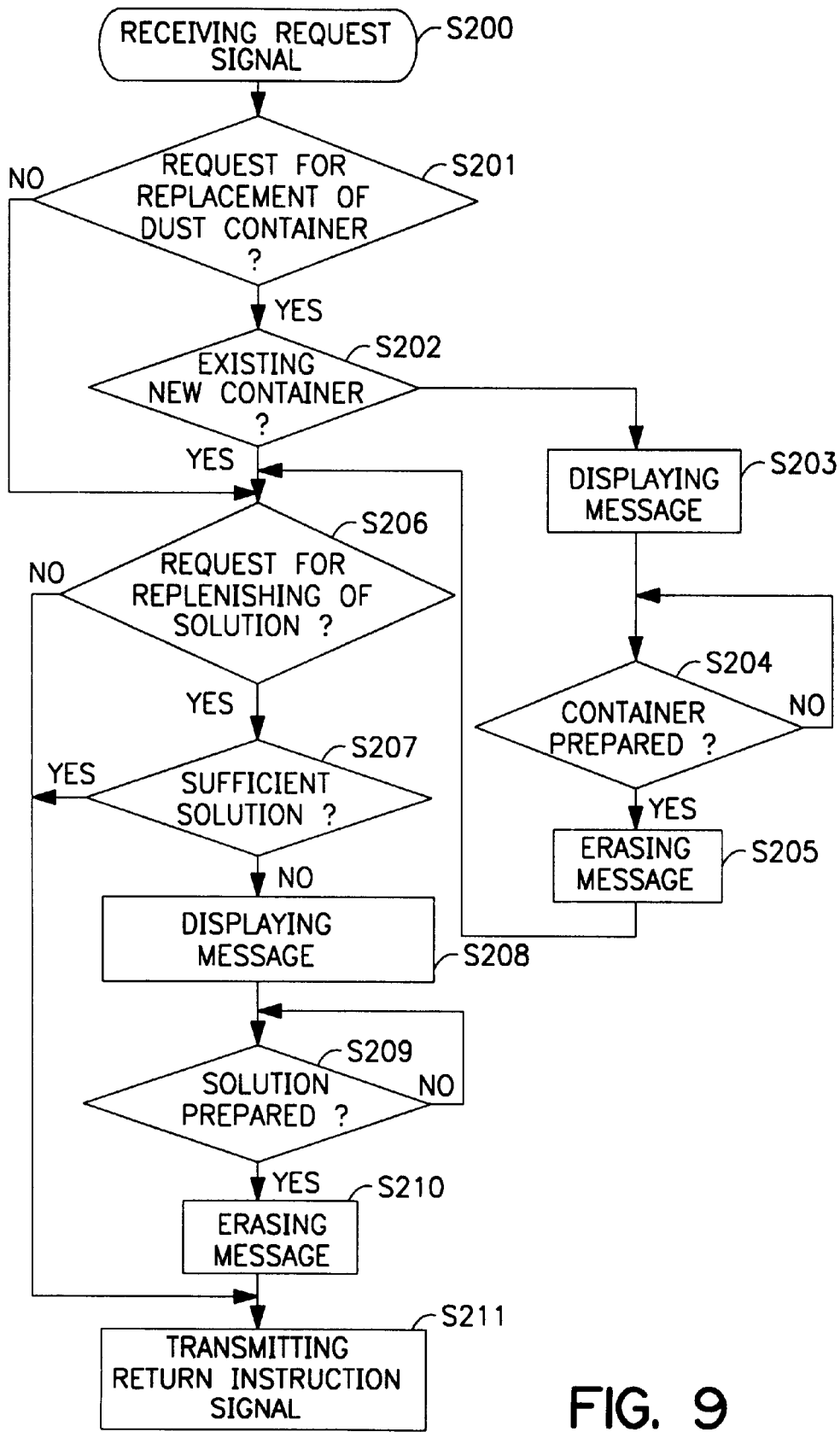

The routine in FIG. 9 is executed only when a signal requesting maintenance has been received (step S200). First, the control unit 24 of the control section 2 determines whether or not a request to replace the dust container has been received from the control unit 14 of the mobile work robot 1 (step S201). Where a request to replace the dust container has not been received, the process advances to step S206. Where a request to replace the dust container has been received, the control unit 24 determines whether or not there is a replacement dust container in the control section 2 (step S202). Where there is one, the process advances to step S206. Where there is not a replacement dust container in the control section 2, the message "Please prepare a replacement dust container" or the like is displayed on the display unit 25B by the control of the input/output unit 25 (step S203), and then, when it is determined that a replacement dust container has been prepared (step S204), the control unit 24 erases the display on the display unit 25B through the control of the input/output unit 25 (step S205), whereupon the process advances to step S206.

In step S206, the control unit 24 determines whether or not a request to replenish the solution comprising a disinfectant, etc., has been received from the control unit 14. Where a request to replenish the solution has not been received, the process advances to step S211. Where a request to replenish the solution has been received, it is determined whether or not there is a sufficient amount of supply solution in the control section 2 (step S207). Where there is a sufficient amount of supply solution, the process advances to step S211. Where there is not a sufficient amount of supply solution, the message "Please prepare supply solution" or the like is displayed in the display unit 25B through the control of the input/output unit 25 (step S208). When it is determined that supply solution has been prepared (step S209), the control unit 24 erases the display in the display unit 25B through the control of the input/output unit 25 (step S210), whereupon the process advances to step S211.

In step S211, control unit 24 sends a return instruction signal to the control unit 14 of the robot 1 through the control of the communication unit 23.

When the robot 1 has returned to the control section 2 after the above routines are carried out, maintenance of the robot 1 by the control section 2 is performed. While replacement of the dust container and replenishment of the solution comprising a disinfectant, etc., were used as examples of parameters governing the maintenance in the example shown with regard to FIGS. 8 and 9 above, the maintenance can involve the replacement of the cleaning members 121 and/or the battery 27.

The control unit 14 of the robot 1 detects problems in the moving unit 11, the working unit 12 and the communication unit 13, such as a temperature increase in the motors or a failure of the rotational angle detectors, for example, through the input of various sensors mounted on the robot 1. When any of these problems is detected, the control unit 14 immediately stops all movement and performance of all tasks. The control unit 14 of robot 1 then notifies the control unit 24 of control section 2 of the existence of the problem through the control of the communication unit 13, whereupon the robot 1 enters a wait state to wait for an instruction.

The control unit 24 of the control section 2 determines the nature of the problem, and where the recovery of the robot 1 at its current position would be difficult, it sends an instruction to the robot 1 to move to the control section 2 through the control of the communication unit 23. Where it would also be difficult for the robot 1 to move to the station, the control unit 24 displays the message "Return difficult" or the like on the display unit 25B through the control of the input/output unit 25.

The control unit 24 of the control section 2 controls the robot cleaning unit 21, the robot maintenance unit 22 and the communication unit 23 independently. Where an instruction is input from the input/output unit 25, it carries out control based on the instruction. Further, where a signal is received from the control unit 14 of the robot 1, the control unit 24 of the control section 2 sends an instruction to the robot control unit 14 as described above or performs control tasks such as the operation of the robot cleaning unit 21 or the operation of the robot maintenance unit 22 of the control section 2, based on the information received.

The cleaning and disinfection of the robot 1 is carried out before the onset of performance of tasks, after the completion of performance of tasks or at prescribed intervals after the performance of tasks has begun. The counting of time is performed using a timer built into the microcomputer of the control unit 24. The timing of the cleaning and disinfection is set through user input by means of the operation panel 25A. Where cleaning and disinfection are to be performed at prescribed intervals after the performance of tasks has begun, the user may set the intervals using the operation panel 25A. The setting should be such that the cleaning and disinfection of the robot 1 is unconditionally carried out before the performance of tasks has begun, for example, where no manual setting is made by a user. The user also may set, by means of the operation panel 25A, the parameters regarding the maintenance performed by the robot maintenance unit 22 when the robot 1 is cleaned and disinfected. Maintenance parameters thus set are executed before the cleaning and disinfection of the robot 1 has begun.

Where cleaning and disinfection of the robot 1 are set to be performed at prescribed intervals after the performance of tasks has begun, the control unit 24 sends a return instruction to the control unit 14 at prescribed intervals after the performance of tasks has begun through the control of the communication unit 23. Upon receiving the return signal, the control unit 14 of the robot 1 suspends the performance of tasks through the control of the working unit 12, and then sends to the control unit 24 of the control section 2 information regarding the current position at which the robot 1 stopped the performance of tasks. The control unit 24 stores this information regarding the current position in the RAM of the microcomputer. The control unit 14 then moves the robot 1 to the control section 2 through control of the moving unit 11.

After cleaning, disinfection and maintenance of the robot 1 are completed, the control unit 24 of the control section 2 sends the information regarding the position at which the performance of tasks was suspended, the information having been stored in the RAM, to the control unit 14 of the robot 1. The control unit 14 controls the moving unit 11 with reference to this information regarding the position at which the performance of tasks was suspended, and returns the robot 1 to the position at which the performance of tasks was suspended. The control unit 14 then controls moving unit 11 and working unit 12 and resumes the performance of tasks. Using the system of this embodiment, since the performance of tasks is reliably resumed even if the robot 1 returns to the control section 2 during the performance of tasks, the tasks can be performed without any problems even if the area that must be cleaned is very large. As described above, the solution level sensor that detects the amount of the solution in the tank of the spray device is connected to the microcomputer of the control unit 24. When a solution amount insufficient signal is received from the solution level sensor, the microcomputer displays the message "Please replenish the cleaning solution" or the like in the display unit 25B through the control of the input/output unit 25. Where it is necessary to clean and disinfect the robot 1 when there is a shortage of the cleaning solution, a return signal is sent to the robot 1 only after the cleaning solution is replenished by the user.

The operation to replace the wiping members by means of the wiping member replacing unit 22B will now be explained as a first embodiment of the maintenance of the robot 1 by the robot maintenance unit 22 of the control section 2.

Figure 3:
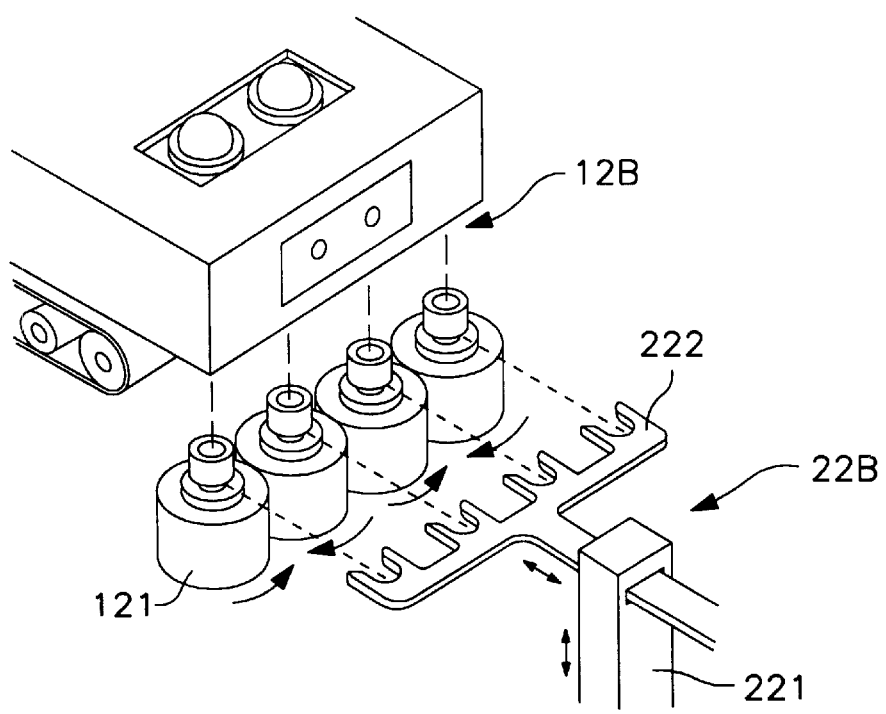
FIG. 3 is a drawing showing a wiping member replacing unit and wiping unit in accordance with the present invention.

FIG. 3 shows an external view of the wiping member replacing unit 22B of the control section 2 and the wiping unit 12B of the robot 1. The wiping unit 12B has wiping members 121, each of which comprises a soft object such as a sponge or a brush, and a support tool. The cleaning solution released onto the floor is spread on the floor by rotating these soft objects while pressing them onto the floor. The wiping members 121 are fixed to mounting members (not shown in the drawings) of the wiping unit 12B by means of snap fixing. The wiping members 121 and the mounting members are configured such that they cannot rotate independently from each other. The cleaning solution may be released onto the soft objects instead of being released onto the floor.

The wiping member replacing unit 22B removes used wiping members 121 from the robot 1 main unit and attaches unused wiping members 122. The wiping member replacing unit 22B has a vertical moving unit 221 and a wiping member holding unit 222. The vertical moving unit 221 is mounted on the control section 2 such that it can move vertically. It also holds the wiping member holding unit 222 such that the wiping member holding unit 222 can move horizontally. The vertical movement of vertical moving unit 221 is carried out through a drive means (a motor and gears, for example) not shown in the drawings. The wiping member holding unit 222 has a holding unit at its tip, the holding unit having a configuration similar to comb teeth. The attachment and removal of the wiping members 121 is carried out by means of this holding unit 222. The horizontal movement of the wiping member holding unit 222 is carried out by means of a drive means (a motor and gears, for example) built into vertical moving unit 221 but not shown in the drawings.

The sequence for the replacement of the wiping members 121 will be explained with reference to FIGS. 4(a) through 4(g). First, the control unit 14 of the robot 1 stops the robot 1 at a prescribed position (the position in FIG. 4(a)) inside the shed 26 through the control of the moving unit 11 based on an instruction signal received from the control unit 24 of the control section 2. This is a position at which a wiping member ejection opening 223 located in the wiping member replacing unit 22B is directly under the used wiping members 121 attached to the robot 1. A wiping member storage area 224 is located between vertical moving unit 221 and the wiping member ejection opening 223 and unused wiping members 122 are housed in this storage area 224 in advance.

The control unit 24 of the control section 2 raises the vertical moving unit 221 to a prescribed position through the control of the wiping member replacing unit 22B. The wiping member holding unit 222 is then pushed forward, and the holding unit having a comb teeth configuration is inserted into the grooves of the wiping members 121 (FIG. 4(b)). The vertical moving unit 221 is then lowered to a level where the snaps of the wiping members 121 are disengaged, through which the wiping members 121 are removed from the wiping unit 12B. A part of the thus removed wiping members 121 enters the wiping member ejection opening 223 (FIG. 4(c)). The wiping member holding unit 222 is then moved to the position shown in FIG. 4(d) and the wiping member holding unit 222 and the wiping members 121 become disengaged, as a result of which the wiping members 121 fall into the wiping member ejection opening 223.

Next, after the vertical moving unit 221 is lowered to the lowest position, the wiping member holding unit 222 is moved forward. The comb teeth-like portion of the wiping member holding unit 222 is inserted into the grooves of the unused wiping members 122. Meanwhile, the control unit 14 of the robot 1 controls the moving unit 11 in response to an instruction from the control unit 24 of the control section 2 and moves the robot 1 backward to the position where the part at which the wiping members 122 are attached is directly above the wiping member storage area 224 (FIG. 4(e)).

Figure 4A:
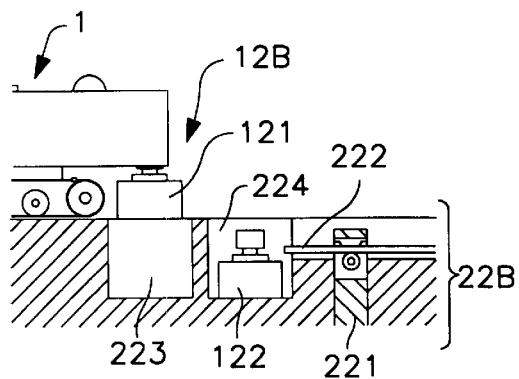
FIGS. 4(a)–4(g) are drawings showing the wiping member replacement sequence in accordance with the present invention.
Figure 4E:
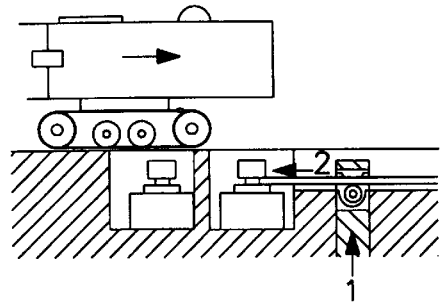
Figure 4B:
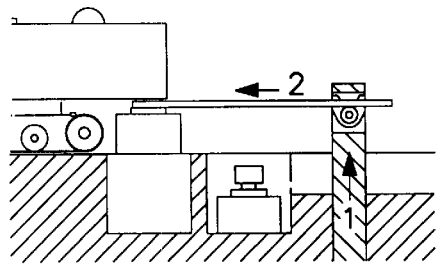
Figure 4F:
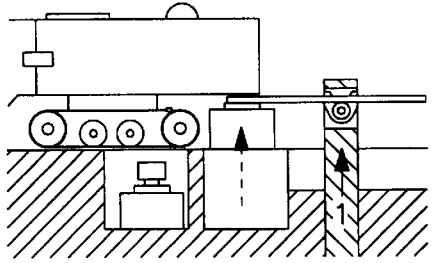
Figure 4C:
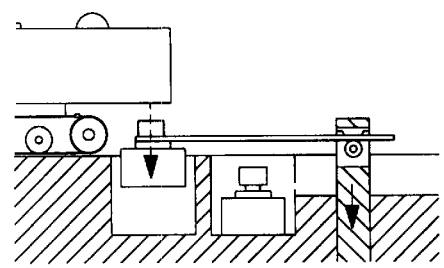
Figure 4G:
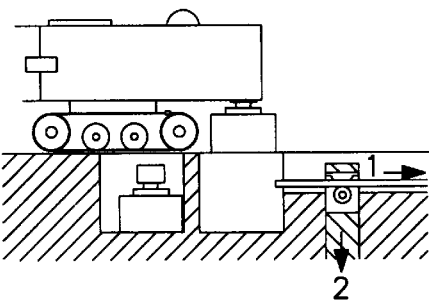
Figure 4D:
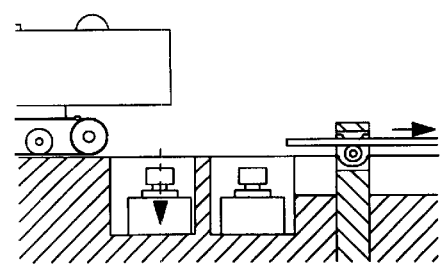

Then, while vertical moving unit 221 is raised, the unused wiping members 122 are attached to the wiping unit 12B of the robot 1 (FIG. 4(f)). With the wiping member holding unit 222 finally moved to the right in the drawing, the wiping member holding unit 222 becomes disengaged from the grooves of the wiping members 122. Subsequently, while the vertical moving unit 221 is lowered, the initial condition is returned to and the wiping member replacement is completed (FIG. 4(g)).

An operation to replace the dust container by the dust container replacing unit 22A will now be explained as a second embodiment of the maintenance of the robot 1 by the robot maintenance unit 22.

Figure 5:
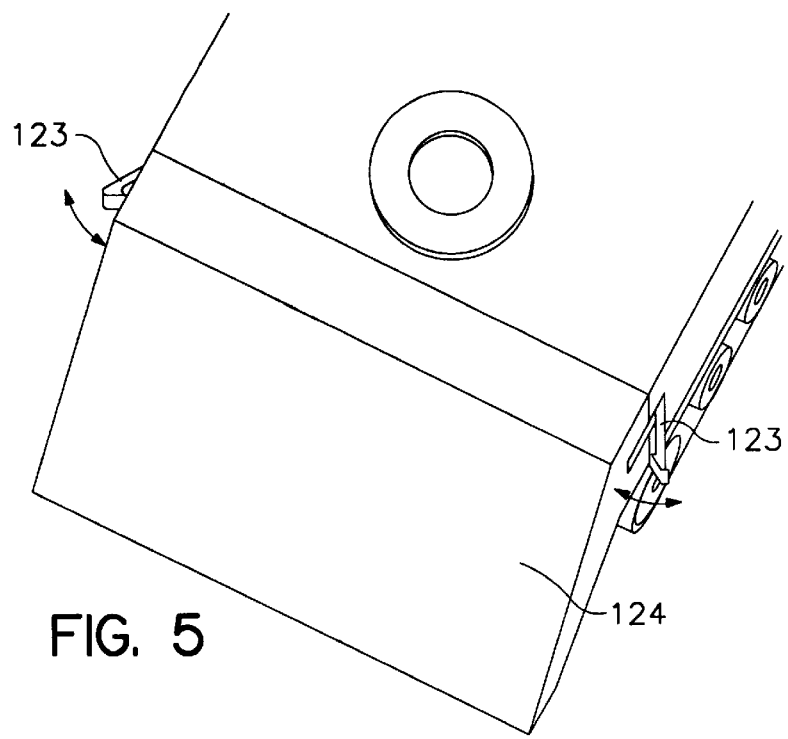
FIG. 5 is a drawing of a dust collecting unit in accordance with the present invention.

FIG. 5 shows an external view of the dust collecting unit 12A of the robot 1. The dust collecting unit 12A is located in the robot 1 main unit. Dust collecting unit 12A comprises a suction unit (not shown in the drawings) comprising a fan and a motor, and a dust container 124 comprising a suction opening and a filter unit mounted behind the opening.

The dust container 124 is fixed to the robot 1 main unit by engaging units 123 located on left and right sides of the robot 1 main unit. The dust container 124 is attached to and removed from the robot 1 main unit by engaging units 123 moving in the directions indicated by arrows. The operation of the engaging unit 123 is performed using a solenoid (not shown in the drawings). This solenoid is operated by means of the dust collecting unit 12A that is controlled by the control unit 14.

The sequence for replacing the dust container 124 will be explained with reference to FIGS. 6(a) through 6(d). The dust container replacing unit 22A is located at the front end of the path in which the robot 1 travels forward (the direction indicated by an arrow in FIG. 6(a)). It removes dust container 124 in which dust has been collected from the robot 1 and simultaneously attaches an unused dust container 125 to the robot 1.

Figures 6A, 6C:
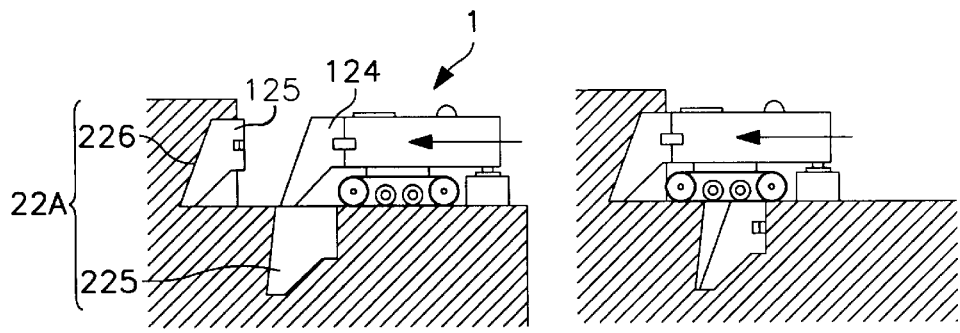
FIGS. 6(a)–6(d) drawings showing the dust container replacement sequence in accordance with the present invention.
Figures 6B, 6D:
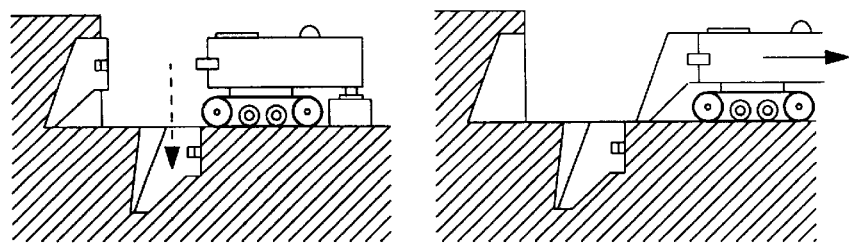

First, the control unit 14 of the robot 1 receives an instruction from the control unit 24 of the control section 2 and stops the robot 1 at the FIG. 6(a) position inside shed 26 through the control of moving unit 11. This is a position at which a dust container ejection opening 225 located in the dust container replacing unit 22A is directly below the used dust container 124 attached to the robot 1.

The dust container storage area 226 is located in front of the robot 1 and the unused dust container 125 is housed in this storage area in advance. The dust container 125 is held on the sides by a supporting member (not shown in the drawings) inside the dust container storage area 226 using an amount of force just sufficient to prevent the dust container 125 from falling down.

After the robot 1 stops at the position shown in FIG. 6(a), the control unit 14 of the robot 1 operates the engaging units 123 so that they will open through the control of the dust collecting unit 12A. Through the opening of the engaging units 123, the dust container 124 falls into the dust container ejection opening 225 (FIG. 6(b)). The construction of the present invention is such that when the dust container 124 is housed in the dust container ejection opening 225, the top surface of the dust container 124 becomes approximately even with the surface on which the robot 1 moves. Therefore, the robot 1 can move on the top surface of the dust container 124.

The control unit 24 of the control section 2 then sends an instruction to the control unit 14 of the robot 1 for the robot 1 to move forward to the position where the robot comes into contact with the unused dust container 125. Upon receiving this instruction, the control unit 14 of the robot 1 moves the robot 1 forward through the control of the moving unit 11. During this movement, the engaging units 123 remain open. When the robot 1 reaches the position where it comes into contact with the unused dust container 125, the control unit 24 of the control section 2 sends an instruction to the control unit 14 of the robot 1 in order to operate the engaging units 123 so that they will close. Upon receiving this instruction, the control unit 14 of the robot 1 closes the engaging units 123 through the control of the dust collecting unit 12A and attaches the dust container 125 to the dust collecting unit 12A of the robot 1 (FIG. 6(c)).

Finally, the control unit 24 of the control section 2 sends an instruction to the control unit 14 of the robot 1 to move the robot 1 backward. Upon receiving this instruction, the control unit 14 of the robot 1 moves the robot 1 backward through the control of the moving unit 11. Through this backward movement, the dust container 125 becomes disengaged from the dust container storage area 226 and dust container replacement is completed (FIG. 6(*d*)).

The engaging units 123 located on the robot are not limited to those that actively open and close as described above. Units that can open and close and which are biased to close by springs, etc., may also be used. Where such engaging units 123 are used, however, a means to open the engaging units 123 should be mounted on the dust container replacing unit 22A so that used the dust container 124 can be removed. When dust container 125 is attached, the engaging units 123 should only be pushed into the dust container 125.

An operation to replenish the cleaning solution by the cleaning solution supply unit 22C will now be explained as a third embodiment of the maintenance of the robot 1 by the robot maintenance unit 22.

Figure 7:
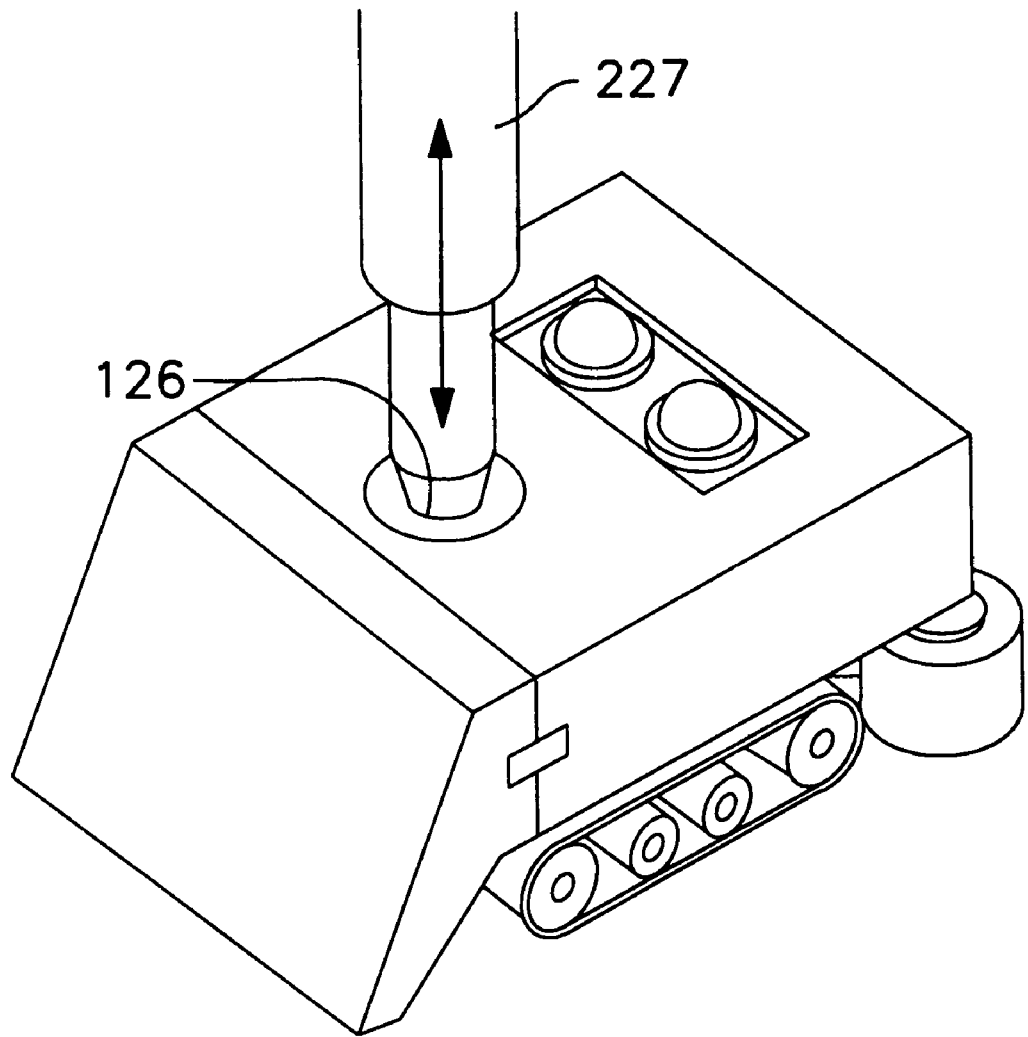
FIG. 7 is a drawing showing the cleaning solution supply operation in accordance with the present invention.

FIG. 7 shows an external view of the robot 1 to which the cleaning solution is being supplied. The cleaning solution supply opening 126 is located on top of the robot 1, and a cleaning solution such as a detergent or disinfectant is supplied from this opening. The cleaning solution thus supplied is stored in the cleaning solution tank (not shown in the drawings) inside the main unit of the robot 1.

The cleaning solution supplying unit 22C comprises a tank (not shown in the drawings) into which cleaning solution is poured in advance, a pump (not shown in the drawings) to pump out this cleaning solution, and the nozzle 227 to eject the cleaning solution thus pumped out. The nozzle 227 is located in the upper area inside shed 26 of the control section 2, and can actively extend upward or downward. In the initial condition, the nozzle 227 is drawn upward.

The sequence for replenishing the cleaning solution will now be explained. The control unit 24 of the control section 2 sends an instruction to the control unit 24 of the robot 1 to move the robot 1 to a position at which cleaning solution supply opening 126 is directly under nozzle 227. Upon receiving this instruction, the control unit 14 moves the robot 1 to the position at which a cleaning solution supply opening 126 is directly under the nozzle 227 through the control of moving unit 11. Then the control unit 24 of the control section 2 extends the nozzle 227 through the control of cleaning solution supply unit 22C and inserts the tip of the nozzle 227 into the cleaning solution supply opening 126. The cleaning solution supply opening 126 has a valve that is normally closed and prevents the cleaning solution from leaking out. When the nozzle 227 is inserted into the cleaning solution supply opening 126, the valve opens, enabling the supply of the cleaning solution.

After the nozzle 227 is inserted into cleaning solution supply opening 126, the control unit 24 of the control section 2 sends out the cleaning solution from the tank to the nozzle 227 by means of the pump through the control of the cleaning solution supply unit 22C, and supplies the cleaning solution to the robot 1.

When the cleaning solution is supplied into the tank of the robot 1 and reaches a prescribed level, the second solution level sensor mounted in the tank sends out a solution full signal to the control unit 14 of the robot 1. In response to this signal, the control unit 14 sends a signal that the tank is full to the control unit 24 of the control section 2. Upon receiving this signal, the control unit 24 stops the pump through the control of the cleaning solution supply unit 22C. The control unit 24 then causes the nozzle 227 to be drawn up to the initial position. The valve closes due to the nozzle 227 disengaging from the cleaning solution supply opening 126, whereupon the replenishment of the cleaning solution is completed.

An operation to charge the battery by the battery charging unit 22D will now be explained as a fourth embodiment of the maintenance of the robot 1 by the robot maintenance unit 22. The robot 1 has a built-in battery 27. At the rear of the main unit of the robot 1 is the charging terminal 127 (see FIG. 2), and the battery 27 is charged by this charging terminal 127 being electrically connected to a power supply terminal (not shown in the drawings) inside the shed 26 of the control section 2.

As described above, the communication between the communication units 13 and 23 consists of wireless communication such as infrared communication, but the communication units may be made as wired communication devices.

Furthermore, an explanation was given with the example of the built-in battery 27 in the robot 1 as the power source for the robot 1, but power may also be supplied to the robot 1 main unit through a cable from a power source inside the control section 2. In this case, the power source for the robot 1, in place of the battery charging unit 22D, is located in the control section 2.

In addition, while only one unit of the robot 1 was used in the embodiments described above, two or more robots 1 may be cleaned, disinfected, maintained and controlled by one control section 2. Cases involving two or more robots 1 handled by one control section 2 includes, for example, a case where cleaning of a large area is performed by two or more robots 1. In this case, the work time may be shortened by two or more robots 1 simultaneously performing tasks. Another case would involve a the robot 1 that performs dust collecting only, a the robot 1 that performs wiping only, a the robot 1 that performs waxing only, etc., for example. In this case, each the robot 1 should be equipped with only the devices necessary for the performance of its task, so that the robot 1 main unit may be reduced in size.

Where two or more robots 1 are handled by one control section 2 as described above, the control section 2 sequentially sends return signals to robots 1 while checking the state of occupancy of the shed 26. The timing of the issuance of return signals is based on the parameters set by the user by means of the input/output unit 25. However, when it becomes time to perform cleaning, disinfection and maintenance of the second robot 1 while the first robot 1 is still being cleaned, disinfected and maintained in the control section 2, for example, the return signal to the second robot 1 is sent after the cleaning, disinfection and maintenance of the first robot 1 is completed.

If it is arranged such that the second robot 1 arrives in the vicinity of the control section 2 at the time when the cleaning, disinfection and maintenance of the first robot 1 is completed, the cleaning, disinfection and maintenance of the robots 1 can be performed more efficiently. Since the control unit 24 of the control section 2 can check the current position of the second robot 1, it can calculate the time necessary for the second robot 1 to return to the control section 2. Further, since the time required for the cleaning, disinfection and maintenance of the robots 1 by the control section 2 is approximately constant, the approximate time at which the cleaning, disinfection and maintenance currently being performed will be finished can be calculated. Therefore, the timing for the issuance of a return signal to the second robot 1 can be calculated, through which efficient cleaning, disinfection and maintenance can be achieved.

Where a maintenance request signal has been received from one robot 1, the control section 2 checks the state of occupancy of the shed 26, and if shed 26 is vacant, the control section 2 sends a return signal to that robot 1 and if the shed 26 is occupied, it sends a standby signal to that robot 1, such that a return signal may be sent to that robot 1 when the shed 26 becomes vacant.

The performance of tasks by the mobile work robot system of the present invention is not limited to the cleaning of floors. The present invention may be applied to the performance of such tasks as the monitoring of a room, fire extinguishing and the marking of a floor at certain distances (used when the floor plan is displayed during construction, for example).

The control section 2 is constructed as a station equipped with the control unit 24, the communication unit 23 and the input/output unit 25 in the embodiments described above. However, the station may be comprised of the robot cleaning unit 21 and the robot maintenance unit 22 only, and a control unit that performs the control of the robot 1 may be placed in the robot 1 itself. The control of the robot cleaning unit 21 and the robot maintenance unit 22 located in the station may be performed by the robot 1 as well.

The robot cleaning unit 21 and the robot maintenance unit 22 may also be located in separate stations.

As described above, in the present invention, a mobile work robot that actually performs tasks and a station having a maintenance means that performs maintenance of the mobile work robot are used so that functions are separated and the minimum functions necessary for the performance of tasks and the minimum amounts of consumable goods necessary for one session of task performance are mounted on the mobile work robot, with all other functions and consumption supplies being mounted on the maintenance means, and therefore, the mobile work robot may be made small in size, enabling the robot to work in small areas, and since the station also works as a station to control the moving means of the mobile work robot, the mobile work robot may be controlled so that it moves to the station when maintenance of the mobile work robot is required.

Further, because cleaning and maintenance of the mobile work robot are performed by a cleaning means and a maintenance means mounted on the station without human contact, the worker has less to do, and microorganisms, dust, etc., that stick to the mobile work robot due to human contact can be prevented from entering the room.

The present invention has been described by way of exemplary embodiments to which the present invention is not limited. The metes and bounds of the invention is set out in the claims appended hereto.

I claim:

1. A mobile robot control system comprising:
   a mobile robot having a moving mechanism for moving said mobile robot, and having a working mechanism which executes a predetermined work;
   a station provided separate from said mobile robot, said station having a maintenance portion for maintaining said mobile robot;
   detecting means for detecting whether maintenance of working mechanism is necessary; and
   control means for controlling said moving mechanism to move said mobile robot to said maintenance portion when said detecting means detects maintenance is necessary.

2. A mobile robot control system as claimed in claim 1, wherein said detecting means is provided in said mobile robot.

3. A mobile robot control system as claimed in claim 2, wherein said detecting means includes a sensor.

4. A mobile robot control system as claimed in claim 1, wherein said control means is provided in said mobile robot.

5. A mobile robot control system as claimed in claim 1, wherein said work mechanism includes a storage unit for supplies.

6. A mobile robot control system as claimed in claim 5, wherein said supplies are consumable goods.

7. A mobile robot control system as claimed in claim 6, wherein the consumable goods are supplied to said working mechanism at said maintenance portion.

8. A mobile robot control system as claimed in claim 7, further comprising:
   second detecting means for detecting an absence of the consumable goods in said maintenance portion; and
   warning means for warning in response to the detection of said second detecting means.

9. A mobile robot control system as claimed in claim 8, wherein said warning means includes a display.

10. A mobile robot control system as claimed in claim 6, wherein said consumable goods are replaceable.

11. A mobile robot control system as claimed in claim 10, wherein the consumable goods in said working mechanism is replaced with new consumable goods provided in said maintenance portion.

12. A mobile robot control system as claimed in claim 11, further comprising:
   second detecting means for detecting absence of the new consumable goods in said maintenance portion; and
   warning means for warning in response to the detection of said second detecting means.

13. A mobile robot control system as claimed in claim 12, wherein said warning means includes a display.

14. A mobile robot control system as claimed in claim 10, wherein said storage unit for storing the consumable goods in said working mechanism is replaced with a new storage unit storing a new supply of consumable goods provided in said maintenance portion.

15. A mobile robot control system as claimed in claim 1, wherein said control means controls said moving mechanism after the lapse of a predetermined time from a previous maintenance operation.

16. A mobile robot control system as claimed in claim 15, further comprising input means for input the predetermined time.

17. A mobile robot control system as claimed in claim 1, further comprising:
   a maintenance mechanism provided in said maintenance portion, said maintenance mechanism executing the maintenance of said mobile robot; and
   second control means for controlling said maintenance mechanism so that said maintenance mechanism executes the maintenance after the arrival of said robot to said maintenance portion.

18. A mobile robot control system as claimed in claim 17, wherein the maintenance executed by said maintenance mechanism is cleaning of said mobile robot.

19. A mobile robot control system as claimed in claim 17, wherein the maintenance executed by said maintenance mechanism is replacement of a part of said working mechanism with a new part of said working mechanism.

20. A mobile robot control system comprising:

a mobile robot having a moving mechanism by which said mobile robot is moved, said mobile robot further having a first supply which is replaceable;

a station provided separate from said mobile robot;

a second supply provided in said station;

detecting means for detecting whether maintenance of said first supply is necessary; and control means for controlling said moving mechanism to move said mobile robot to said station when said detecting means detects that maintenance is necessary.

21. A mobile robot control system as claimed in claim 20, wherein said control means controls said robot to replace said first supply with said second supply.

22. A mobile robot control system as claimed in claim 20, further comprising:

second detecting means for detecting absence of said second supply in said station; and warning means for warning in response to the detection of said second detecting means.

23. A mobile robot control system as claimed in claim 22, wherein said warning means includes a display.

24. A mobile robot comprising:

a moving mechanism by which said robot is moved;

a working mechanism which executes a predetermined work;

a detector which detects whether maintenance of said working mechanism is necessary; and a controller which controls said moving mechanism to move said robot to a predetermined portion of a maintenance station in accordance with the detection of said detector.

25. A mobile robot as claimed in claim 24, wherein said working mechanism executes the predetermined work with consuming liquid, and said detector detects an amount of the liquid.

26. A mobile robot as claimed in claim 24, wherein said working mechanism executes the predetermined work with collecting dust in a storage, and said detector detects an amount of the dust in storage.

* * * * *